United States Patent [19]

Holt et al.

[11] Patent Number: 5,137,882
[45] Date of Patent: Aug. 11, 1992

[54] STEROIDAL 3-ACETIC ACID DERIVATIVES AS 5-ALPHA-REDUCTASE INHIBITORS

[76] Inventors: Dennis A. Holt; Mark A. Levy; Brian W. Metcalf, all of P.O. Box 7929, Philadelphia, Pa. 19101

[21] Appl. No.: 535,807

[22] Filed: Jun. 11, 1990

[51] Int. Cl.$^5$ .......................... A61K 31/58; C07J 9/00; C07J 71/00
[52] U.S. Cl. .................................. 514/182; 514/172; 552/557; 552/599; 552/601; 552/611
[58] Field of Search ............... 552/557, 599, 610, 601, 552/611; 514/182, 172

[56] References Cited

U.S. PATENT DOCUMENTS

| 3,129,233 | 4/1964 | Deghenghi | 552/651 |
|---|---|---|---|
| 4,191,759 | 3/1980 | Johnston et al. | 514/177 |
| 4,191,795 | 3/1980 | Johnston et al. | 514/177 |
| 4,307,086 | 12/1981 | Tax | 514/182 |
| 4,317,817 | 3/1982 | Blohm et al. | 514/150 |
| 4,361,578 | 11/1982 | Alig et al. | 514/462 |
| 4,377,584 | 3/1983 | Rasmusson et al. | 514/284 |

FOREIGN PATENT DOCUMENTS 0289327 11/1988 European Pat. Off. .

OTHER PUBLICATIONS

Yvon et al; Chemical Abstract vol. 75, 1971 #1789Z.
Hoechst; Chemical Abstract vol. 69, 1968 #97001m.
Hsia and Voight, J. Invest. Dermat. 62:224–227 (1974).
Robaire et al., J. Steroid Biochem. 8:307–310 (1977).
Blohm, T. R., et al., Biochem. Biophys. Res. Comm. 95:273–280 (1980).
Liang, T., et al., J. Steroid Biochem. 19, 385–390 (1983).
Petrow, V., et al., Steroids 38:121–140 (1981).
Cacchi et al., Tet. Letters, 26: 1109–1112 (1985).
Neeman, J. Chem. Soc. Perkin I 2297 (1972).
Neeman, J. Chem. Soc. Perkin I 2300 (1972).
Hylarides, J. Org. Chem. 49, 2744 (1984).
Brooks et al., Steroids: 47:1–19 (Jan., 1986).
Ross et al., J. Org. Chem., 29: 27845–2785 (1964).

Primary Examiner—Mukund J. Shah
Assistant Examiner—Y. N. Gupta
Attorney, Agent, or Firm—Wayne J. Dustman; Stephen Venetianer; Edward T. Lentz

[57] ABSTRACT

Invented are 3-acetic acid-steroidal compounds, pharmaceutical compositions containing the compounds, and methods of using these compounds to inhibit steroid 5α-reductase including using these compounds to reduce prostate size and to treat prostatic adenocarcinoma. Also invented are intermediates used in preparing these compounds.

13 Claims, No Drawings

STEROIDAL 3-ACETIC ACID DERIVATIVES AS 5-ALPHA-REDUCTASE INHIBITORS

FIELD OF THE INVENTION

The present invention relates to certain novel 3-substituted acetic acid analogues of steroidal synthetic compounds, pharmaceutical compositions containing these compounds, and methods for using these compounds to inhibit mammalian steroid 5-α-reductase.

DESCRIPTION OF RELATED ART

The class of steroidal hormones known as androgens is responsible for the physical characteristics that differentiate males from females. Of the several organs that produce androgens, the testes produce these hormones in the greatest amounts. Centers in the brain exert primary control over the level of androgen production. Numerous physical manifestations and disease states result when ineffective control results in excessive androgen hormone production. For example, acne vulgaris, seborrhea, female hirsutism, benign prostatic hypertrophy and male pattern baldness are correlated with elevated androgen levels. Additionally, the reduction of androgen levels has been shown to have a therapeutic effect on prostate cancer.

Testosterone is the principal androgen secreted by the testes and is the primary androgenic steroid in the plasma of males. It now is know that 5-α-reduced androgens are the active hormones in some tissues such as the prostate and sebaceous gland. Circulating testosterone thus serves as a prohormone for dihydrotestosterone (DHT), its 5-α-reduced analogue in these tissues but not in others such as muscle and testis. Steroid 5-α-reductase is a NADPH dependent enzyme that converts testosterone to DHT. The importance of this enzyme in male development was dramatically underscored by discovery of a genetic steroid 5-α-reductase deficiency in male pseudohermaphrodites. Imperator McGinley, J., et al., (1979), *J. Steroid Biochem.* 11:637-648

Recognition of the importance of elevated DHT levels in many disease states has stimulated many efforts to synthesize inhibitors of this enzyme. Several known steroid 5-α-reductase inhibitors have been disclosed.

The first inhibitor described was a 17-β-carboxylic acid by Hsia and Voight in 1973. *J. Invest. Dermat.* 62:224-227. A secosteroid was the next inhibitor to be described and also has found utility as an affinity label for 5-α-reductase. Robaire, B., et. al., (1977), *J. Steroid Biochem.* 8:307-310. A diazoketone has been reported as a potent, time dependent inhibitor of steroid 5-α-reductase. Blohm, T. R., et. al. (1980), *Biochem. Biophys. Res. Comm.* 95:273-280; U.S. Pat. No. 4,317,817, Mar. 2, 1982. A compound that is exemplary of a group of 4 aza steroid inhibitors of steroid 5-α-reductase is described in U.S. Pat. No. 4,377,584 which issued March 22, 1983, and in Liang, T., et. al., (1983), *J. Steroid Biochem.* 19, 385-390. A 6-methylene steroid al.so has been shown to be a time dependent inactivator of steroid 5-α-reductase. 7 Petrow, V., et. al., (1981), *Steroids* 38:121-140.

Other steroid 5-α-reductase inhibitors also have been described. U.S. Pat. No. 4,361,578 which issued Jun. 2, 1986, describes a class of homosteroid enzyme inhibitors. U.S. Pat. No. 4,191,759 discloses amides of 17-β-carboxy-4-androsten 3-one that are active as steroid 5-α-reductase inhibitors. Japanese Patents J60146855 A and J60116657 A disclose various aniline derivatives having numerous activities including 5-α-reductase inhibiting activity. Japanese Patent I60142941 A discloses phenyl substituted ketones having 5-α-reductase inhibiting activity and European Patent EP173516-A discloses various phenyl substituted amides having similar activity. Shiseido referenced terpene derivatives that are active inhibitors of steroid 5-α-reductase. Japanese Patent, No. J59053417 A.

SUMMARY OF THE INVENTION

The present invention resides in the discovery that steroid 5-α-reductase is inhibited by certain substituted homo carboxylic acid analogues of steroidal synthetic compounds. The compounds are potent enzyme inhibitors.

Presently preferred compounds of the invention and compounds used in the invented pharmaceutical compositions and the invented methods include:

(E) 17β-(N,N diisopropylcarboxamide) androst-4-ene-3 ylidene acetic acid,

17β-(N,N diisopropylcarboxamide) androst-3,5-diene-3 acetic acid, (Z) 17β-(N,N diisopropylcarboxamide) androst 4-ene-3-ylidene acetic acid, 17β-(N,N diisopropylcarboxamide)-5α-androst-2-ene-3 acetic acid, (Z) 17β-(N,N diisopropylcarboxamide)-5α-androst-3 ylidene acetic acid, 17β-(N,N-diisopropylcarboxamide)-5-androst-3-ene-3-acetic acid, and 17β-N-t-butylcarboxamide-5-α-androst 2 ene 3 acetic acid.

In a further aspect of the invention there are provided novel intermediates and novel processes useful in preparing the presently invented 5-α-reductase inhibiting compounds.

The invention also is a method for inhibiting 5-α-reductase activity in mammals, including humans, that comprises administering internally to a subject in need thereof an effective amount of a presently invented 5-α-reductase inhibiting compound.

Included in the present invention are pharmaceutical compositions comprising a pharmaceutical carrier and compounds useful in the methods of the invention.

DETAILED DESCRIPTION OF THE INVENTION

The presently invented compounds that inhibit 5-α-reductase have the following Formula (I):

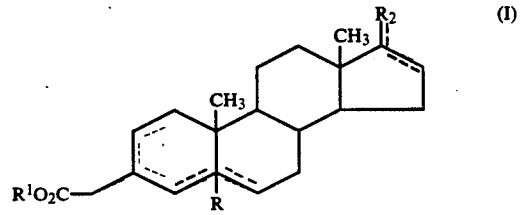

in which:

the compound has optional double bonds where indicated by the broken lines, provided the A-ring has up to 2 double bonds, the 3-position substituent does not ave a double bond when the A ring has a $C_2-C_3$ or $C_3-C_4$ double bond, the A-B rings do not have adjacent double bonds and the D ring does not have a $C_{16}-C_{17}$ double bond when $R^2$ represents two substituents or A divalent substituent;

$R^1$ is H or $C_{1-8}$ alkyl;

R is absent when there is a $C_4$-$C_5$ or $C_5$-$C_6$ double bond, or present as an alpha hydrogen; and $R^2$ is hydrogen; and (1) α-hydrogen, α-hydroxyl, or α-acetoxy and/or

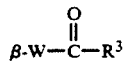 (a)

where W is a bond or $C_{1-12}$ alkyl, and $R^3$ is (i) hydrogen, (ii) hydroxyl, (iii) $C_{1-8}$ alkyl, (iv) hydroxy$C_{1-8}$alkyl, (v) $C_{1-8}$ alkoxy, (vi) $NR^4R^5$, where $R^4$ and $R^5$ are each independently selected from hydrogen, $C_{1-8}$ alkyl, $R^4$ and $R^5$ taken together with the nitrogen to which they are attached represent a 5-6 membered saturated ring comprising up to one other heteroatom selected from oxygen and nitrogen, or (vii) $OR^6$, where $R^6$ is hydrogen, alkali metal, benzyl, or (b) β-Alk-$OR^7$, where Alk is $C_{1-12}$ alkyl, and $R^7$ is (i) phenyl $C_{1-6}$ alkylcarbonyl, (ii) $C_{5-10}$ cycloalkylcabonyl, (iii) benzoyl, (iv) $C_{1-8}$alkoxycarbonyl, (v) aminocarbonyl, or $C_{1-8}$ alkyl substituted amino carbonyl, (vi) hydrogen, or (vii) $C_{1-8}$alkyl, (2) =CH—W—CO—$R^3$ or =CH—W—$OR^7$, where W is a bond or $C_{1-12}$ and $R^3$ and $R^7$ have the same meaning as above and $R^7$ also is hydrogen or $C_{1-20}$ alkylcarbonyl;

(3)

where the dashed bond replaces the 17-α-hydrogen, (4) α-hydrogen and β-NHCOR$^8$ where $R^8$ is $C_{1-12}$ alkyl or β-$NR^4R^5$ where $R^4$ and $R^5$ have the same meaning as above, (5) α-hydrogen and β-cyano, (6) α-hydrogen and β-tetrazolyl, or (7) keto;

or a pharmaceutically acceptable salt thereof.

As used herein, unless otherwise specified, $C_{1-n}$ alkyl means a straight or branched hydrocarbon chain having 1 to n carbons. Also, preferred among the presently invented compounds are those having Formula (II):

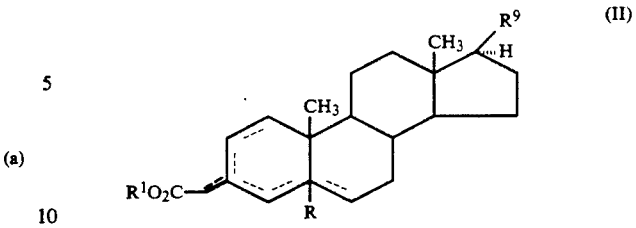

in which:

the compound has optional double bonds where indicated by the broken lines, provided the A ring has up to 2 double bonds, the 3-position substituent does not have a double bond when the A ring has a $C_2$-$C_3$ or $C_3$-$C_4$ double bond and the A-B rings do not have adjacent double bonds;

$R^1$ is H or $C_{1-8}$alkyl;

R is absent when there is a $C_4$-$C_5$, $C_5$-$C_6$ double bond, or present as an alpha hydrogen; and $R^9$ is (a) $CH(CH_3)CH_2OR^{10}$ wherein $R^0$ is H or $C_{1-6}$ alkyl, or (b) $CONR^{11}R^{12}$ wherein $R^{11}$ and $R^{12}$ independently are H or $C_{1-8}$alkyl; or a pharmaceutically acceptable salt thereof.

Particularly preferred are Formula (II) compounds in which the A ring has a $C_2$-$C_3$ double bond.

Compounds of Formula (I) in which $R^1$=H are included in the pharmaceutical compositions of the invention and used in the methods of the invention. Compounds of Formula (I) in which $R^1$=$C_{1-8}$ Alkyl are useful intermediates of the invention.

As used above and throghout the remainder of the specification and claims the carbons of the steroid nucleus are numbered and the rings and lettered as follows:

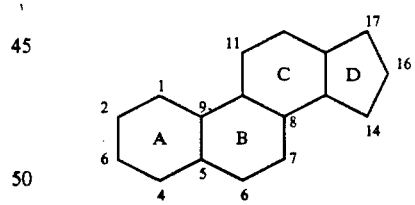

Formula (I) compounds are prepared as shown in Schemes I through IV. $R^{13}$ is $R^2$ or moieties which can be converted to those of $R^2$ by known chemical reactions such as described in J. Fried and J. Edwards, *Organic Reactions in Steroid Chemistry*, Pub: Van Nostrand Reinhold Company (1972) provided that $R^{13}$ does not include any such moieties that render inoperative the Schemes I to IV processes. As demonstrated in the following Examples, reactions to convert $R^{13}$ to $R^2$ are performed on products of the synthetic pathways of Schemes I through IV or, where appropriate or preferable, on certain intermediates in these synthetic pathways

SCHEME I

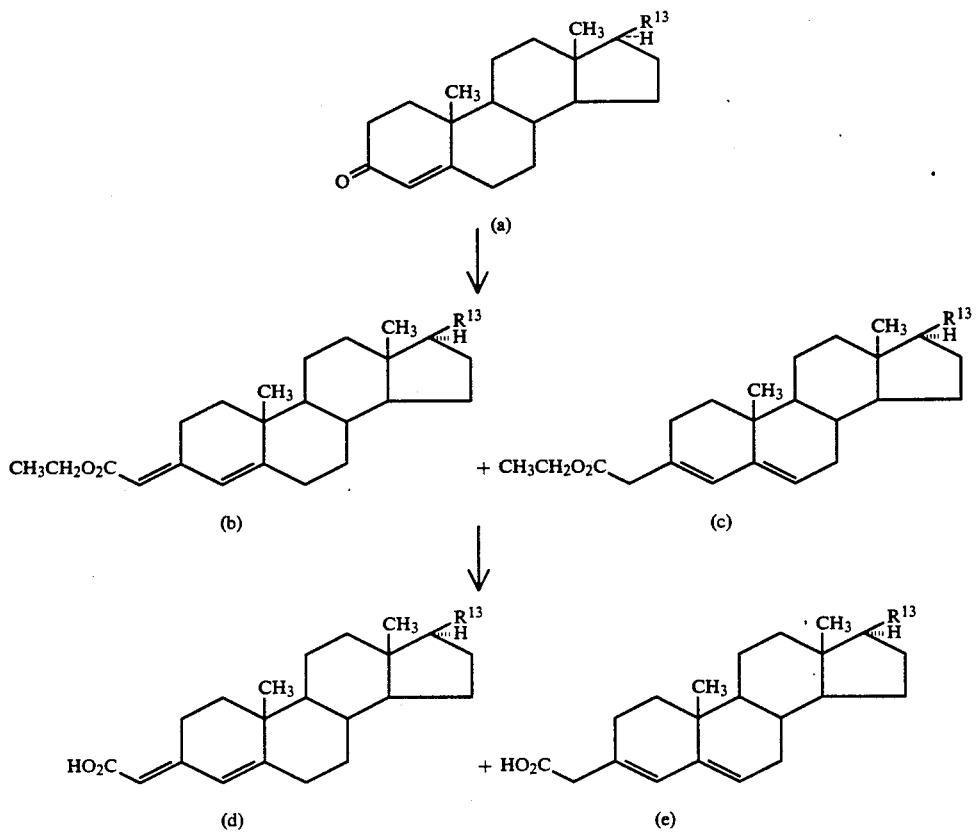

Scheme I depicts formation of Formula (I) compounds which have a $C_4$-$C_5$ double bond or $C_3$-$C_4$ and $C_5$-$C_6$ double bonds. The starting 4-ene 3 one compounds (a) are known and readily available and are synthesized from available precursors using known procedures as described in European Patent Application 88303878.8. According to Scheme I, a solution of a 4-ene 3 one compound (a) and a phosphorane precursor, preferably methyl diethylphosphonoacetate, are dissolved in an appropriate organic solvent, preferably ethanol, under anhydrous conditions, to form a reaction mixture. A mixture of Formula (b) and (c) compounds then is prepared by stirring the reaction mixture with an appropriate base such as a sodium alkoxide base, preferably sodium ethoxide, at reflux for three hours. The addition of a base, preferably potassium carbonate, to a mixture of Formula (b) and (c) compounds dissolved in a suitable organic solvent, preferably refluxing 10:1 ethanol water, followed by addition of a strong acid, preferably aqueous HCl, yields a mixture of Formula (d) and (e) compounds which are separated upon chromatography.

SCHEME II

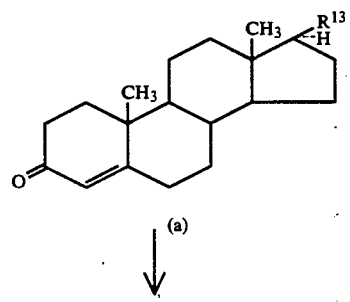

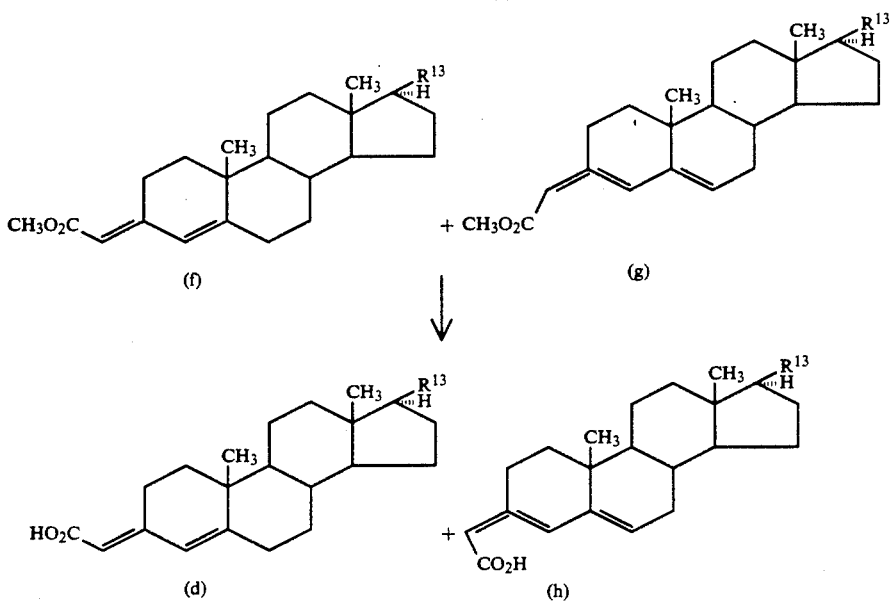

Scheme II illustrates synthesis of Formula (I) compounds with (E) and (Z) ylidene-acetic acid derivatives at the 3 position. The starting materials are the Formula (a) 4-ene 3 one compounds from Scheme I. According to Scheme II, a Formula (a) compound dissolved in an appropriate organic solvent, preferably tetrahydrofuran (THF), is added to a reaction mixture consisting of 1,1-dibromo-2-chloro-2-methoxy ethane and an alkyl lithium reagent, preferably N butyllithium, in an appropriate organic solvent, preferably tetrahydrofuran (THF), at a temperature of $-100°$ C. to $-30°$ C., preferably $-78°$ C., followed by addition of a strong acid, preferably sulfuric acid, to yield a mixture of Formula (f) and (g) compounds. The mixture of Formula (f) and (g) compounds was hydrolyzed in a manner analogous to the procedure used in Scheme I to yield a mixture of Formula (d) and Formula (h) compounds which are separated upon chromatography and fractional recrystallization.

SCHEME III

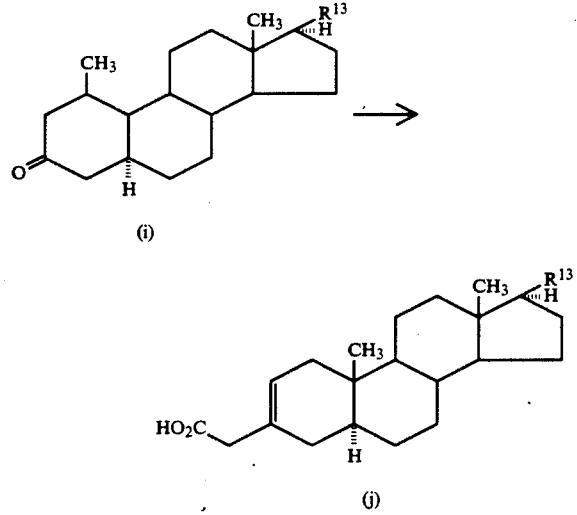

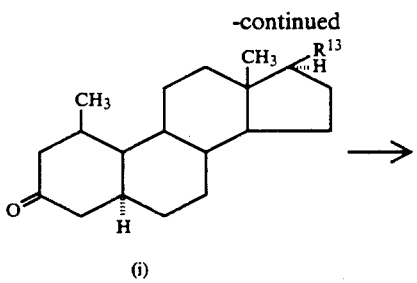

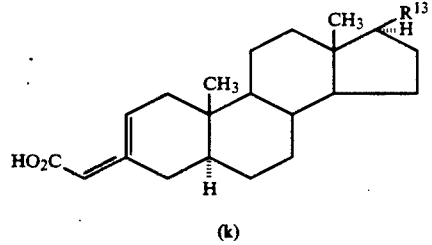

Scheme (III) depicts formation of Formula (I) compounds which have a $C_2-C_3$ double bond or have a saturated steroidal ring system. The starting 3-one compounds (i) are known and readily available or are synthesized from available precursors using known procedures as described in European Patent Application 88303878.8. Substitution of Formula (i) compounds for Formula (a) compounds in Scheme I yields Formula (j) compounds.

Compounds (k) are prepared from compounds (i) by substituting an appropriate base, preferably sodium hydride (in DMF), for sodium ethoxide in a process analogous to the procedures used in Scheme (I).

SCHEME IV

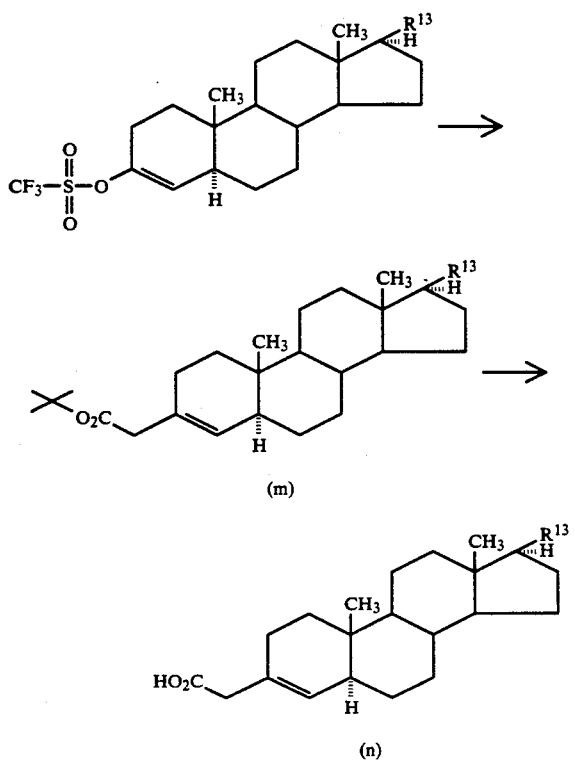

Scheme IV illustrates synthesis of Formula (I) compounds which have a $C_3-C_4$ double bond and a saturated B ring. Compounds (1) are obtained by known procedures from 3-one precursors as described in European Patent Application 88303878.8. According to Scheme IV, to a palladium (II) compound, preferably bis (triphenyl phosphine) palladium (II) chloride, and diisobutyl aluminum hydride in a suitable organic solvent such as tetrahydrofuran is added a formula (1) compound. An alkyl halo acetate, preferably t butyl-α-(bromozinc) acetate, in an aprotic solvent, preferably hexamethyl phosphoramide, is added to yield Formula (m) compounds. The addition of a base, preferably aqueous lithium hydroxide, to a Formula (m) compound in a suitable organic solvent, preferably refluxing 1:1 methanol-tetrahydrofuran yields Formula (n) compounds.

Pharmaceutically- acceptable acid addition salts of the compounds of the invention containing a basic group are formed where appropriate with organic or inorganic acids by methods known to the art. For example, the base is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the acid addition salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts. Pharmaceutically acceptable base addition salts of compounds of the invention containing an acidic group are prepared by known methods from organic and inorganic bases include nontoxic alkali metal and alkaline earth bases, for example, calcium, sodium, and potassium hydroxide; ammonium hydroxide, and nontoxic organic bases such as triethylamine, butylamine, piperazine, and (trihydroxymethyl)methylamine.

Because the pharmaceutically active compounds of the present invention inhibit steroid 5-α-reductase activity, they have therapeutic utility in treating diseases and conditions wherein decreases in DHT activity produce the desired therapeutic effect. Such diseases and conditions include acne vulgaris, seborrhea, female hirsutism, prostate diseases such as benign prostatic hypertrophy and prostatic adenocarcinoma and male pattern baldness. The activity of several compounds of the invention was tested for efficacy in inhibiting human steroid 5-α-reductase using tissue from hyperplastic human prostates. In determining potency in inhibiting the human enzyme, the following procedure was employed:

Frozen human prostates were thawed and minced into small pieces (5 mm³) The tissue was homogenized in 3 to 5 volumes of 20 mM potassium phosphate, pH 6.5, buffer containing 0.33M sucrose, 1 mM dithiothreitol, and 50 μM NADPH with a Brinkmann Polytron (Sybron Corporation, Westbury, N.Y.). The solution was subjected to sonication for 3 to 5 minutes with a Sonifier (Branson Sonic power Co.) followed by hand homogenization in a glass-to glass Dounce homogenizer (Kontes Glass Company, Vineland, N.J.). Prostatic particles were obtained by differential centrifugation at 600 or 1000×g for 20 minutes and 140,000×g for 60 minutes at 4° C. The pellet obtained from the 140,000×g centrifugation was washed with 5 to 10 tissue volumes of the buffer described above and recentrifuged at 140,000×g. The resulting pellet was suspended in 20 mM potassium phosphate buffer, pH6.5, containing 20% glycerol, 1 mM dithiothreitol, and 50 mM NADPH The suspended particulate solution was stored at −80° C.

A constant amount of [$^{14}$C]-testosterone (52 to 55 mCi/mmol, New England Nuclear, Boston, Md.) in ethanol and varying amounts of the potential inhibitor in ethanol were deposited in test tubes and concentrated to dryness in a SAVANT Speed Vac. To each tube was added buffer, 20 μl of 10 mM NADPH and an aliguot of prostatic particulate solution to a final volume of 1.0 ml of 50 mM sodium citrate, pH 5.0. After incubating the solution at 37° C. for 20 to 30 minutes the reaction was quenched by the addition of 4 ml ethyl acetate and 0.25 μmol each of testosterone, dihydrotestosterone, androstanediol, and androstanedione as carriers. The organic layer was removed to a second test tube and evaporated to dryness in a Speed Vac. The residue was dissolved in 20 to 30 μl chloroform, spotted on an individual lane of a 20×20 cm prechannelled silica gel TLC plate (Si 250F PA, Baker Chemical) and developed twice with acetone:chloroform (1:9). The radiochemical content localized in the substrate and the products was determined with a BIOSCAN Imaging Scanner (Bioscan, Inc., Washington, D.C.). The percent of recovered radiolabel converted to product was calculated, from which enzyme activity was determined. All incubations were conducted such that no more than 12% of the substrate (testosterone) was consumed.

The experimentally obtained data was computer fitted to a linear function by plotting the reciprocal of the enzyme activity (1/velocity) against the variable inhibitor concentration (Dixon, M. (1953), *Biochem. J.*, 55, 170). The value for the inhibition constant (Ki) was calculated from known procedures (Levy, M. (1989), *Biochemistry*, 29:2815–2824).

Compounds within the scope of this invention have been tested and have been shown to have activity from 35 to >10,000 $K_i$(nM), these compounds are potent inhibitors of human steroid 5-α-reductase.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically-active compounds in a pharmaceutical dosage unit as described above will be as efficacious, nontoxic quantity selected from the range of 0.1–1000 mg/kg of active compound, preferably 1–100 mg/kg. The selected dose is administered to a human patient in need of steroid 5-α-reductase inhibition from 1–6 times daily, topically, orally, rectally, by injection, or continuously by infusion. Oral dosage units for human administration preferably contain from 1 to 500 mg of active compound. Parenteral administration, which uses lower dosages is preferred. Oral administration, at high dosages, however, also can be used when safe and convenient for the patient.

The method of this invention of inhibiting steroid 5-α-reductase activity in mammals, including humans, comprises administering internally to a subject in need of such inhibition an effective steroid 5-α-reductase inhibiting amount of a pharmaceutically active compound of the present invention.

Contemplated equivalents of Formula I compounds are compounds otherwise corresponding thereto wherein substituents have been added to any of the unsubstituted positions of the Formula (I) compounds or the methyl group at C-13 is absent or replaced by $C_{1-4}$alkyl provided such compounds have the pharmaceutical utility of Formula (I) compounds.

The following examples illustrate preparation of Formula (I) compounds and pharmaceutical composition containing these compounds. The examples are not intended to limit the scope of the invention as defined hereinabove and as claimed below.

EXAMPLE 1

(E) 17β-(N,N-Diisoprop-vlcarboxamide) androst-4-ene-3-ylidene-acetic acid and

17-β-(N,N Diisopropylcarboxamide) androst 3,5-diene-3-acetic acid (i) (E)-Ethyl-17β-(N,N-Diisopropylcarboxamide)-androst-4-ene-3-ylidene acetate and
Ethyl-17-β-(N,N-Diisopropylcarboxamide)-androst-3,5-diene3-acetate Sodium ethoxide solution prepared from Na (800 mg, 33 mmol) and absolute ethanol (20 mL) was added to a mixture of 17-β-(N,N-diisopropylcarboxamide)-androst-4-ene-3-one (4.1 g, 10.3 mmol), absolute ethanol (20 mL) and methyl diethylphosphonoacetate (6.87 g, 33 mmol). After for 3 hours, ethanol was removed in vacuo. The residue was treated with 10% aqueous HCl and the resulting mixture was extracted with diethyl ether. The ethereal extract was washed with water, 5% aqueous NaHCO$_3$, water, brine, dried and concentrated. The residue was chromatographed on silica gel eluting with 10% ethyl acetate in hexane to yield 4.0 g (83%) of the mixture of the title compounds.

(ii) (E)-17-β-(N,N-Diisopropylcarboxamide)-androst-4-ene-3-ylidene-acetic acid and
17-β-(N,N-Diisopropylcarboxamide)-androst-3,5-diene-3-acetic acid A mixture of (E) Ethyl 17β-(N,N Diisopropyl-carboxamide)-androst-4-ene-3-acetate and ethyl 17β-(N,N-Diisopropylcarboxamide)-androst-3,5-diene-3-acetate (4.0 g, 8.5 mmol) and potassium carbonate (4.0 g, 29 mmol) suspended in 275 mL of 10:1 ethanol water was heated at reflux for 18 hours. Ethanol was removed in vacuo. The residue was acidified with 10% aqueous HCl, diluted with water and extracted with ethyl acetate. The extract was washed with water, brine, dried and concentrated. Purification by flash chromatography eluting with 15% ethyl acetate and 1% glacial acetic acid in hexane afforded (E) 17-β-(N,N-Diisopropylcarboxamide)-androst-4-ene-3-ylidene-acetic acid ($R_f$ 0.5), MP 308° C. Further elution gave 17-β-(N,N-Diisopropylcarboxamide) androst-3,5-diene3-acetic acid ($R_f$ 0.4) MP, 205°–207° C.

EXAMPLE 2

(E) 17-β-(N,N-Diisopropylcarboxamide)-androst-4-ene-3-ylidene-acetic acid and
(Z)-17-β-(N,N-Diisopropylcarboxamide)-androst-4-ene 3-ylidene-acetic acid (i) (E) Methyl-17-β-(N,N-Diisopropylcarboxamide)-androst-4-ene3-ylidene-acetate and
(Z) Methyl 17β-(N,N-Diisopropylcarboxamide)-androst-4-ene3-yildene acetate 1,1-Dibromo2-chloro2-methoxy-ethane (1.72 g, 6.87 mmol; prepared according to the procedure described by R. H. Smithers, *Synthesis*, 556 (1985) was added to n BuLi (5.8 mL of 2.5 M solution in hexane, 14.5 mmol) at −78° C. over a 30 minute period under argon. The mixture was stirred at −78° C. for 30 minutes and warmed up to −20° C. 17β-(N,N-Diisopropylcarboxamide)-androst4-ene-3-one suspended in THF (15 mL) was added slowly over a 10 minute period. The resulting mixture was stirred for 20 minutes at −20° C and warmed up to 0° C. then H$_2$SO$_4$ (2M, 5 mL) was added and stirred for 6 hours at ambient temperature. The reaction mixture was diluted with ethyl acetate, washed with brine, saturated aqueous NaHCO₃, dried and concentrated. The residue was chromatographed on silica gel eluting with 10% ethyl acetate in hexane to yield a mixture of the title compounds.

(ii) (E) 17-β-(N,N-Diisopropylcarboxamide)-androst-4-ene-3-ylidene-acetic acid and (Z)-17-β-(N,N-Diisopropylcarboxamide)-androst-4-ene 3-ylidene-acetic acid (E) 17-β-(N,N-Diisopropylcarboxamide)-androst-4-ene ylidene-acetic acid and (Z) 17-β-(N,N-Diisopropylcarboxamide)-androst-4-ene-3-ylidene-acetic acid (MP substituting a mixture of (E)-Methyl-17-β-(N,N-Diisopropyl carboxamide)-androst-4ene-3-ylidene-acetate and (Z) Methyl 17-β-(N,N-Diisopropylcarboxamide)-androst-4-ene3ylidene-acetate for (E)-ethyl-17-β-(N,N-Diisopropyl carboxamide)-androst-4-ene-4-ylidene-acetate and Ethyl 17β-(N,NDiisopropylcarboxamide)-androst-3,5-diene-3-acetate.

EXAMPLE 3

17β-(N,N-Diisopropylcarboxamide)-5-α-androst-2-ene-3-acetic acid (i) Ethyl 17(N,N-Diisoproplcarboxamide)-5α-androst-2-ene-3-acetate The title compound was prepared according to Example 1(i) by subsistuting 17-β-(N,N-diisopropylcarboamide)

(ii) 17β-(N,N-Diisopropylcarboxamide)-5α-androst-2-ene-3-acetic acid

The title compound was prepared according to Example 1 (ii) by substituting Ethyl 17β-(N,N-Diisopropylcarboxamide) 5α-androst-2-ene-3-acetate for the mixture of (E) Ethyl-17β-(N,N-Diisopropylcarboxamide)-androst-4-ene-3-ylidene-acetate and Ethyl 17β-(N,N-Diisopropyl carboxamide) androst 3,5-diene-3-acetate. Microanalysis confirmed title compound as a 1/4 hydrate: theory C, 75.03; H, 10 23; N, 3.13 found C, 74.82; H, 10.42; N, 2.97.

EXAMPLE 4

(Z)-17β-N,N-Diisopropvlcarboxamide)-5α-androst-3-ylidene-acetic acid (i)(Z)Ethyl 17β-(N,N-Diisopropylcarboxamide)-5α-androst-3-ylidene-acetate The title compound was prepared according to Example 3 (i) by substituting sodium hydride in N,N-Dimethylformamide for sodium ethoxide in ethanol.

(ii) (Z) 17β-(N,N-Diisopropylcarboxamide)-5α-androst-3 ylidene-acetic acid

The title compound (MP. 270° C.) was prepared according to Example 3 (ii) by substituting (Z) Ethyl 17β-(N,N-Diisopropylcarboxamide) 5α-androst-3-ylidene-acetate for Ethyl-17β-(N,N-Diisopropylcarboxamide)-5α-androst-2-ene-3-acetate.

EXAMPLE 5

17β-(N.N-Diisopropylcarboxamide)-5α-androst-3-ene-3-acetic acid (i) t-butyl-17β-(N,N-Diisopropylcarboxamide)-5α-androst-3-ene3-acetate Bis (triphen-ylphosphine) Palladium (II) chloride (345 mg, 0.492 mmol) was suspended in 2.5 ml of dry tetrahydrofuran at 0° C. under an argon atmosphere. Diisobutyl aluminum hydride (0.85 ul, 1.0N solution in toluene) was added dropwise via syringe. After 5 minutes, 3-[[(trifluoromethyl)-sulfonyl]oxy]-5β-androst3-ene-17β-(N,N-diisopropylcarboxamide) (750 mg, 1.405 mmol) in 15 ml of dry tetrahydrofuran was added to the reaction mixture. After 10 minutes t-butyl α-(bromozinc)acetate (930 mg, 3.57 mmol; prepared according to D. A. Cornforth, A. E. Opara, and G. Read, *J. Chem. soc.* (c), 2799 (1969)) in 4 ml of hexamethylphosphoramide was added and the reaction mixture was allowed to warm to room temperature and stir for six hours. The reaction mixture was then washed with 10% hydrochloric acid and brine; dried over magnesium sulfate and evaporated. Chromatography on silica gel eluting with 10% ethyl acetate in hexane yielded t-butyl-17β-(N,N-Diisopropyl carboxamide) 5α-androst-3-ene-3-acetate 425 mg (61%).

(ii) 17(N,N-Diisopropylcarboxamide)-5α-androst-3-ene3-acetic acid t-Butyl 17β-(N,N-Diisopropylcarboxamide) 5α-androst-3-ene-3-acetate (100 mg, 0.200 mmol) and aqueous lithium hydroxide (2 ml of 1.0N solution) in 10 ml of a 1:1 mixture of methanol tetrahydrofuran under an argon atmosphere was heated at reflux overnight. The resulting solution was washed with water, brine, dried and concentrated. Purification by flash chromatography eluting with 10% methanol in chloroform afforded 17β-(N,N-Diisopropylcarboxamide) (N,N-Diisopropylcarboxamide) 5α-androst-3-ene-3-acetic acid 45 mg (51%) MP 236 239° C.

EXAMPLE 6

17β-t-butylcarboxamide-5α-androst-2-ene-3-acetic acid

The title compound is prepared according to Example 3 (i ii) by substituting 17β-N-t-butylcarboxamide5α-androst-3-one for 17β-(N,N-Diisopropylcarboxamide) 5α-androst 3-one. (MP. 189°-190° C.)

EXAMPLE 7

An oral dosage form for administering Formula (I) compounds is produced by screening, mixing, and filling into hard gelatin capsules the ingredients in the proportions shown in Table I below.

TABLE I

| Ingredients | Amounts |
| --- | --- |
| 17β-(N,N-Diisopropylcarboxamide)-5α-androst-2-ene-3-acetic acid | 50 mg |
| Magnesium Stearate | 5 mg |
| Lactose | 75 mg |

EXAMPLE 8

The sucrose, calcium sulfate dihydrate and Formula (I) compound shown in Table II below, are mixed an granulated in the proportions shown with a 10% gelatin solution. The wet granules are screened, dried, mixed with the starch, talc and stearic acid, screened and compressed into a tablet.

TABLE II

| Ingredients | Amounts |
| --- | --- |
| 17β-(N,N-Diisopropylcarboxamide)-5α-androst-2-ene-3-acetic acid | 100 mg |
| Calcium Sulfate Dihydrate | 150 mg |
| Sucrose | 20 mg |
| Starch | 10 mg |
| Talc | 5 mg |
| Stearic acid | 3 mg |

EXAMPLE 9

17β-(N,N-Diisopropylcarboxamide)-5α-androst-2-ene-3-acetic acid, 75 mg, is dispursed in 25 ml of normal saline to prepare an injectable preparation.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound represented by the formula:

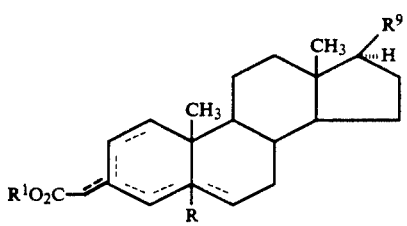

(II)

in which:
the compound has optional double bonds where indicated by the broken lines, provided the A ring has up to 2 double bonds, the 3-position substituent does not have a double bond when the A-ring has a $C_2$–$C_3$ or $C_3$–$C_4$ double bond and the A–B rings do not have adjacent double bonds;
$R^1$ is H or $C_{1-8}$ alkyl;
R is absent when there is a $C_4$–$C_5$ or $C_5$–$C_6$ double bond, or present as an alpha hydrogen; and
$R^9$ is
 (a) $CH(CH_3DH_2OR^{10}$ wherein $R^{10}$ is H or $C_{1-6}$ alkyl, or
 (b) $CONR^{11}R^{12}$ wherein $R^{11}$ and $R^{12}$ independently are H or $C_{1-8}$ alkyl; or a pharmaceutically acceptable salt thereof.

2. A compound of claim 1 that is:
17β-(N-N-diisopropylcarboxamide)-5α-androst-2-ene-3-acetic acid.

3. A compound of claim 1 that is:
(E)-17β-(N,N-diisopropylcarboxamide)-androst-4-ene-3-ylidene-acetic acid,
17β-(N,N diisopropy-lcarboxamide) androst-3,5-diene-3-acetic acid,
(Z) 17β(N,N diisopropylcarboxamide)-androst-3-ylidene-acetic acid,
(Z) 17(N,N diisopropylcarboxamide)-5α-androst-3 ylidene-acetic acid, or
17β-(N,N diisoprop-ylcarboxamide)-5α-androst-3-ene-3-acetic acid.

4. A pharmaceutical composition comprising a suitable pharmaceutical carrier and a compound of claim 1 in which $R^1$ is H.

5. A composition of claim 4 wherein the compound is:
17β-(N,N-diisopropylcarboxamide)-5α-androst-2-ene3-acetic acid.

6. A composition of claim 4 wherein the compound is:
 (E) 17β-(N,N-diisopropylcarboxamide)-androst-4-ene-3-ylidene-acetic acid,
17β-(N,N-diisopropylcarboxamide)-androst-3,5-diene3-acetic acid,
 (Z) 17β-(N,N-diisopropylcarboxamide)-androst-4-ene-3-ylidene-acetic acid,
 (Z) 17β-(N,N-diisopropylcarboxamide)-androst-3-ylidene-acetic acid, or
17β-(N,N-diisopropylcarboxamide)-androst-3-ene-3-acetic acid.

7. A method of inhibiting steroid 5α-reductase activity in a mammal, in need thereof, that comprises administering internally to the subject an effective amount of a compound of claim 1 in which $R^1$ is H.

8. A method of claim 7 wherein the compound is 17β-(N,N-diisopropylcarboxamide)-5α-androst-2-ene-3-acetic acid.

9. A method of claim 7 where in the compound is:
 (E) 17β-(N,N-diisopropylcarboxamide)-androst-4-ene-3-ylidene-acetic acid,
17β-(N,N-diisopropylcarboxamide)-androst-3,5-diene-3-acetic acid,
 (Z)-17β-(N,N-diisopropylcarboxamide)-androst-4-ene-3-ylidene-acetic acid,
 (Z)-17β-(N,N-diisopropylcarboxamide)-5α-androst-3-ylidene-acetic acid, or
17β(N,N-diisopropylcarboxamide)-5α-androst-3-ene-3-acetic acid.

10. A compound of claim 1 that is 1762 -N-t-butylcarboxamide -5α-androst-2-ene3-acetic acid.

11. A composition of claim 4 wherein the compound is 17β-N-t-butylcarboxamide-5α-androst-2-ene-3-acetic acid.

12. A method of claim 7 wherein the compound is N-t-butylcarboxamide-5α-androst2-ene-3-acetic acid.

13. A compound of claim 1 wherein the A-ring has a $C_2$–$C_3$ double bond.

* * * * *

UNITED STATES PATENT AND TRADEMARK OFFICE
CERTIFICATE OF CORRECTION

PATENT NO. : 5,137,882
DATED : August 11, 1992
INVENTOR(S) : Holt, Levy, Metcalf It is certified that error appears in the above-identified patent and that said Letters Patent is hereby corrected as shown below:

In claim 1, column 15, line 36, replace "$CH(CH_3DH_2OR^{10}$" with --- $CH(CH_3)CH_2OR^{10}$ ---.

In claim 3, column 15, line 50, replace "(Z)17ß(N,N diisopropylcarboxamide)-androst-3-yli-dene-acetic acid" with --- (Z)-17ß-(N,N-diisopropylcarboxamide)-androst-4-ene-3-ylidene-acetic acid ---.

In claim 3, column 16, line 1, replace "17(N,N diisopropylcarboxamide)-5α-androst -3ylidene-acetic acid" with --- 17ß-(N,N-diisopropylcarboxamide)-5α-androst-3-ylidene-acetic acid ---.

In claim 6, column 16, line 20, replace "17ß-(N,N-diisopropylcarboxamide)-androst-3-ylidene-acetic acid" with --- 17ß-(N,N-diisopropylcarboxamide)-5α-androst-3-ylidene acetic acid ---.

In claim 6, column 16, line 22, replace "17ß-(N,N-diisopropylcarboxamide)-androst-3-ene-3-acetic acid" with --- 17ß-(N,N-diisopropylcarboxamide)-5α-androst-3-ene-3-acetic acid ---.

UNITED STATES PATENT AND TRADEMARK OFFICE
CERTIFICATE OF CORRECTION

PATENT NO. : 5,137,882
DATED : August 11, 1992
INVENTOR(S) : Dennis A. Holt, et al.

It is certified that error appears in the above-indentified patent and that said Letters Patent is hereby corrected as shown below:

In claim 10, column 16, line 42, replace "1762-N-t-butylcarboxamide-5α-androst-2-ene3-acetic acid" with --- 17ß-N-t-butylcarboxamide-5α-androst-2-ene-3-acetic acid ---.

Signed and Sealed this

Fifth Day of April, 1994

Attest:

Attesting Officer

BRUCE LEHMAN

Commissioner of Patents and Trademarks